United States Patent [19]

Schlosberg et al.

[11] Patent Number: 5,430,108
[45] Date of Patent: Jul. 4, 1995

[54] POLYOL ESTER PVC PLASTICIZERS

[75] Inventors: Richard H. Schlosberg, Bridgewater, N.J.; John R. Hooton, Baton Rouge, La.; Leonard G. Krauskopf, Baton Rouge, La.; Francisco M. Benitez, Baton Rouge, La.; James D. Gerald, Baton Rouge, La.

[73] Assignee: Exxon Chemical Patents Inc., Wilmington, Del.

[21] Appl. No.: 182,913

[22] Filed: Jan. 14, 1994

[51] Int. Cl.⁶ .................. C08K 5/10; C07C 67/40
[52] U.S. Cl. .................. 524/311; 524/310; 524/315; 524/321; 524/377
[58] Field of Search .............. 524/311, 315, 377, 321, 524/310; 560/129

[56] References Cited

U.S. PATENT DOCUMENTS

| 4,421,886 | 12/1983 | Worschech et al. | 524/310 |
| 4,605,694 | 8/1986 | Walker | 524/292 |
| 4,826,633 | 5/1989 | Carr et al. | 252/56 S |

FOREIGN PATENT DOCUMENTS 1618586 4/1971 Germany.

Primary Examiner—Paul R. Michl
Assistant Examiner—Olga Asinovsky
Attorney, Agent, or Firm—R. D. Jordan; J. J. Mahon

[57] ABSTRACT

Plasticized PVC compositions are disclosed which are heat resistant and which exhibit low smoke generation where the plasticizer is a pentaerythritol ester of mixed $C_5$, $C_7$ and $C_9$ alkanoic acids.

5 Claims, No Drawings

POLYOL ESTER PVC PLASTICIZERS

This invention relates to compositions that are useful as plasticizers for thermoplastic polyvinylchloride (commonly referred to as PVC). More particularly, it relates to plasticizers for PVC intended for use in high temperature resistant applications and which are characterized as having low smoke generating properties.

Poly(vinyl chloride), hereafter referred to as PVC, is extensively used in many applications. In use, PVC is plasticized to permit it to be processed into a flexible material. In addition, other additives such as thermal stabilizers, lubricants, pigments, fillers, impact modifiers, and flame retardants are generally employed to produce PVC compositions having desired properties.

Despite its thermal instability, unmodified PVC has relatively good flame retardant properties due to its high chlorine content. However, the plasticizer necessary for flexibility and good processing properties generally increases the flammability of PVC compositions, especially if used at high levels. Moreover, when PVC burns, it produces considerable smoke, and the addition of some flame retardants to plasticized compositions to reduce their flammability generally increases smoke generation upon burning. It is desirable to have a PVC plasticizer which is compatible with the resin and provides to the composition the required physical properties and at the same time exhibits low smoke generating properties, obviating the need for special smoke suppressant additives.

Polyol esters have been used in PVC compositions as disclosed, for example, in U.S. Pat. No. 4,605,694 (issued Aug. 12, 1986 to Walker), where they are taught for use in combination with trimellitate as an extender and secondary plasticizer. U.S. Pat. No. 4,421,886 (issued Dec. 20, 1983 to Worschek et al.) discloses PVC compositions, where the partial ester of pentaerythritol is used in combination with a polybasic lead compound as a stabilizer-lubricant combination. German application 1618586 (published Apr. 1, 1971) in the abstract makes a general disclosure that partial esters of pentaerythritol are useful as plasticizers and stabilizers for polymers.

The present invention is based on the discovery that pentaerythritol, when fully esterified with a mixture of certain alkyl carboxylic acids, provides a heat resistant PVC plasticizer which is compatible with PVC over a range of 20–70 phr (parts by weight per hundred parts by weight of resin), and which exhibits desirable low smoke generating properties when measured in accordance with ASTM E-662.

According to the invention, there has been discovered heat-resistant, low smoke-generating plasticized PVC blended with a plasticizing composition characterized in that the plasticizing composition is in an amount of about 20–70, such as 50–70, e.g., wire formulations are typically 30–35, phr and consists essentially of a pentaerythritol alkanoic acid ester, wherein the alkanoic acid is a mixture of $C_5$, $C_7$, and $C_9$ monocarboxylic alkanoic acids ($C_5$ means five carbon atoms, $C_7$ means seven carbon atoms and $C_9$ means nine carbon atoms), the $C_5$ acid being a straight or branched chain acid and comprising about 0–50 wt. % of the acid mixture, such as 30–50 wt. %, the $C_7$ acid being straight or branched chain, preferably an iso-$C_7$ acid having only one or two methyl branches and comprising about 40–92 wt. % of the acid mixture, and the $C_9$ acid being 3,5,5-trimethylhexanoic acid and comprising about 8–12 wt. % of the acid mixture.

The pentaerythritol alkanoic acid esters useful in accordance with this invention are made by completely esterifying pentaerythritol, using methods well known to those skilled in the art, with the mixture of $C_5$, $C_7$, and $C_9$ monocarboxylic alkanoic acids.

Pentaerythritol used in accordance with this invention is monopentaerythritol or a nfixture of at least 70% by weight monopentaerythritol and one or more polypentaerythritols, such as for example, technical pentaerythritol, which is a mixture of monopentaerythritol and about 12% by weight polypentaerythritols, mostly dipentaerythritol.

Preferably stabilizers, such as for example lead phthalate, are also added during plasticizing to prevent dehydrochlorination and oxidation of the PVC during processing and later use. Other useful additives are known and include, for example, pigments, fillers, and lubricants (i.e., processing aids), which uses depend on the specific PVC application and will be apparent to those skilled in the art.

The term "polyvinyl chloride" as used herein is intended to cover those homo- and copolymer resins of vinyl chloride known to persons of ordinary skill in the art. Generally speaking, copolymers of vinyl chloride (containing up to about 20% of such monomers as vinyl acetate, propylene, ethylene, diethyl maleate, dimethyl fumarate, and other ethylenically unsaturated monomers) are intended to be covered.

The compositions of the plasticized polyvinyl chloride resins of the present invention may be formulated, in addition to the above described plasticizers, with various kinds of additives according to need. For example, additives which contribute to improvement of properties such as heat stability, lubricity, weathering resistance and the like, are exemplified by metal soaps such as calcium stearate, zinc stearate, lead stearate, barium stearate, cadmium stearate and the like, tribasic lead sulfate, dibasic lead phosphite, organotin compounds such as dibutyltin dilaurate, dibutyltin dimaleate, di-n-octyltin mercaptide, dimethyltin mercaptide and the like as a stabilizer, and esters such as butyl stearate, aliphatic acid amides such as ethylene bistearamide, higher fatty acids such as stearic acid and polyethylene waxes as a lubricant, fillers, anti-oxidants, ultraviolet absorbers, anti-static agents, anti-fogging agent, pigments, dye-stuffs, crosslinking aids and the like.

As stabilizers there can be cited, for example, metal soaps (e.g., potassium stearate, zinc stearate, aluminum stearate and the like), inorganic acid salts (e.g., dibasic phosphorous acid salt, dibasic sulfuric acid salt and the like), and organic metal compounds (e.g., dibutyltin maleate, dioctyltin maleate, dioctyltin bis(2-ethylhexyl maleate) and the like as organic tin stabilizer, epoxylated soybean oil, or epoxy resin and the like).

As fillers there can be cited, for example, inorganic fillers (e.g., hydrate silica, calcium carbonate, talc, diatomaceous earth, kaolin clay, sedimented barium sulfate and the like), and organic alloying polymers such as thermoplastic resins (e.g., cellulose-, polyethylene terephthalate-, acrylic rubber- and urethane-based resins).

The lubricant includes various kinds of paraffins and waxes, fatty acid amides, fatty acid esters, fluorohydrocarbons, organic silicones, as well as metal soaps.

The pigment may be of any type as far as it is suited for coloring. There can be used various pigments such as inorganic pigments (e.g., titanium oxide and red oxide) and organic pigments (e.g., carbon black, phthalocyanin blue singly or in the form of a mixture).

EXAMPLES

Pentaerythritol esters were prepared from a mixture composed of 50 wt. % n-$C_5$ acid, 40 wt. % iso-$C_7$ acid, 10 wt. % 3,5,5-trimethylhexanoic acid (ESTER A), 38 wt. % n-$C_5$ acid, 54 wt. % iso-$C_7$ acid, and 8 wt. % 3,5,5-trimethylhexanoic acid (ESTER B).

Both ESTER A and ESTER B were compatible over the range of 20–70 phr when compounded with PVC.

These esters were evaluated for smoke generation in flexible PVC in accordance with ASTM E-662, which compares the smoke generation with a standard plasticizer, diisodecyl phthalate (DIDP), and ESTER A and ESTER B exhibited an average smoke reduction of 12–24% as reported below in Table 1. "DS/g" means density of smoke per gram.

TABLE 1

| Ester | Smoke Density | % Relative to DIDP | Smoke, % Reduction |
| --- | --- | --- | --- |
| DIDP | 45.1 DS/g | — | — |
| A | 34.2 DS/g | 76% | 24% |
| B | 39.8 DS/g | 88% | 12% |

What is claimed is:

1. A plasticized polyvinyl chloride composition exhibiting heat resistant and low smoke generating properties wherein the plasticizer consists of a pentaerythritol ester of a mixture of about 0–50 wt. % of $C_5$ alkyl carboxylic acid, 40–92 wt. % of $C_7$ alkyl carboxylic acid, and 8–12 wt. % of 3,5,5-trimethylhexanoic acid and is present in an amount equal to 20–70 parts per hundred parts of resin.

2. The composition of claim 1 wherein the $C_5$ and $C_7$ acids are methyl branched chain acids.

3. The composition of claim 1 wherein the $C_5$ acid is present in an amount of about 38%, the $C_7$ acid is present in an amount of about 54%, and the 3,5,5-trimethylhexanoic acid is present in an amount of about 8%.

4. The composition of claim 1 wherein the $C_5$ acid is present in an amount of about 50%, the $C_7$ acid is present in an amount of about 40%, and the 3,5,5-trimethylhexanoic acid is present in an amount of about 8%.

5. The composition of claims 1, 2, 3 or 4 wherein the plasticizer is present in an amount of 50–70 parts per hundred parts of resin.

* * * * *